(12) United States Patent
Wilson et al.

(10) Patent No.: US 12,306,160 B2
(45) Date of Patent: May 20, 2025

(54) BINARY GAS PURITY ANALYZER

(71) Applicant: MKS Instruments, Inc., Andover, MA (US)

(72) Inventors: Chad David Wilson, Andover, MA (US); Gerardo A. Brucker, Longmont, CO (US); Junhua Ding, Boxborough, MA (US)

(73) Assignee: MKS Instruments, Inc., Andover, MA (US)

( * ) Notice: Subject to any disclaimer, the term of this patent is extended or adjusted under 35 U.S.C. 154(b) by 704 days.

(21) Appl. No.: 17/452,030

(22) Filed: Oct. 22, 2021

(65) Prior Publication Data

US 2023/0127693 A1 Apr. 27, 2023

(51) Int. Cl.
*G01N 33/00* (2006.01)
*G01F 1/88* (2006.01)

(52) U.S. Cl.
CPC .......... *G01N 33/0031* (2013.01); *G01F 1/88* (2013.01); *G01N 33/0006* (2013.01)

(58) Field of Classification Search
CPC .. G01N 33/0031; G01N 33/0006; G01F 1/88; G01F 1/74; G01F 1/86; G01F 1/8436; G01F 1/36; G01F 1/34; G01F 5/00; G01F 9/00; G01F 15/04; G01F 25/10; G01F 15/02; G01F 1/68; G01F 1/76; G01F 1/50; G01F 1/80; G01F 1/00; G01F 7/00; G01F 7/005; G01F 1/78; F02D 41/0007; F02D 2200/0402; F02D 41/0072; F02M 26/05; F02M 26/06; F02M 26/47; F02M 35/10386
See application file for complete search history.

(56) References Cited

U.S. PATENT DOCUMENTS 4,290,296 A 9/1981 Bredeweg et al.
9,557,744 B2 1/2017 Ding
(Continued)

FOREIGN PATENT DOCUMENTS

CN 109164837 A * 1/2019 ......... G01N 33/0009
JP 2004-246826 A 9/2004
(Continued)

OTHER PUBLICATIONS

Provisional Application and Drawings as filed on Nov. 20, 2020 for U.S. Appl. No. 63/116,599, titled: Method and Apparatus for Pulse Gas Delivery with Pressure Control.
(Continued)

*Primary Examiner* — Eric S. McCall
*Assistant Examiner* — Anthony W Megna Fuentes
(74) *Attorney, Agent, or Firm* — Hamilton, Brook, Smith & Reynolds, P.C.

(57) ABSTRACT

Systems and methods for detecting a composition of a binary gas mixture are provided. Such methods and systems include, with a species-dependent mass flow meter, sensing a mass flow rate of a binary gas mixture comprising gases of differing gas correction factors and, with a species-independent pressure sensor, sensing a total pressure of the binary gas mixture. An output representative of a relative concentration of one gas of the binary gas mixture is provided. The relative concentration is determined as a function of the sensed mass flow rate and the sensed total pressure.

19 Claims, 8 Drawing Sheets

(56) References Cited

U.S. PATENT DOCUMENTS

| | | |
|---|---|---|
| 9,846,074 B2 | 12/2017 | Ding |
| 10,914,717 B2 | 2/2021 | Brucker |
| 2008/0134751 A1 | 6/2008 | Huang |
| 2010/0292934 A1 | 11/2010 | Stark et al. |
| 2013/0092257 A1 | 4/2013 | Yasuda et al. |
| 2014/0202238 A1 | 7/2014 | Henry |
| 2017/0199529 A1 | 7/2017 | Ding |
| 2020/0384238 A1* | 12/2020 | Blunsden ........... B01D 53/0454 |

FOREIGN PATENT DOCUMENTS

| | | | |
|---|---|---|---|
| WO | 2000050890 A1 | 8/2000 | |
| WO | WO-2009002262 A1 * | 12/2008 | ............ A61M 16/12 |
| WO | 2013/109443 A1 | 7/2013 | |
| WO | 2015/123008 A1 | 8/2015 | |
| WO | 2023/069839 A1 | 4/2023 | |

OTHER PUBLICATIONS

International Search Report and Written Opinion for application No. PCT/US2022/077732 with filing date Oct. 7, 2022 dated Jan. 18, 2023.

* cited by examiner

| Gas 1 FS | 2000 | | | Gas 1 Type | N2 | | | |
|---|---|---|---|---|---|---|---|---|
| Gas 2 FS | 2000 | | | Gas 2 Type | O2 | | | |
| Gas 1 SP % | Gas 2 % | Gas 1 Flow | Gas 2 Flow | UUT Sensor V | UUT Flow | UUT T | P1 | P2 |
| 100% | 0% | 2000 | 0 | 0.5777 | 2006.77 | 26.83 | 19.2 | 19.638 |
| 90% | 10% | 1800 | 200 | 0.5779 | 2007.46 | 26.81 | 19.27 | 19.71 |
| 80% | 20% | 1600 | 400 | 0.578 | 2008.04 | 26.82 | 19.34 | 19.78 |
| 70% | 30% | 1400 | 600 | 0.5789 | 2010.86 | 26.83 | 19.41 | 19.853 |
| 60% | 40% | 1200 | 800 | 0.5795 | 2013.44 | 26.83 | 19.49 | 19.928 |
| 50% | 50% | 1000 | 1000 | 0.5802 | 2015.82 | 26.82 | 19.57 | 19.998 |
| 40% | 60% | 800 | 1200 | 0.5813 | 2019.21 | 26.8 | 16.65 | 20.074 |
| 30% | 70% | 600 | 1400 | 0.5816 | 2020.58 | 26.79 | 19.74 | 20.141 |
| 20% | 80% | 400 | 1600 | 0.5827 | 2024.58 | 26.79 | 19.88 | 20.219 |
| 10% | 90% | 200 | 1800 | 0.5838 | 2028.74 | 26.81 | 19.9 | 20.294 |
| 0% | 100% | 0 | 2000 | 0.5857 | 2035.11 | 26.8 | 19.91 | 20.375 |

| Gas 1 FS | 2000 | Gas 1 Type | He | | | | |
|---|---|---|---|---|---|---|---|
| Gas 2 FS | 2000 | Gas 2 Type | N2 | | | | |
| Gas 1 SP % | Gas 2 % | Gas 1 Flow | Gas 2 Flow | UUT Sensor V | UUT Flow | UUT T | P1 | P2 |
| 100% | 0% | 2000 | 0 | 0.5776 | 2006.45 | 25.97 | 19.61 | 19.64 |
| 90% | 10% | 1800 | 200 | 0.5612 | 1948.85 | 25.98 | 19.52 | 19.58 |
| 80% | 20% | 1600 | 400 | 0.5439 | 1888.07 | 25.99 | 19.42 | 19.51 |
| 70% | 30% | 1400 | 600 | 0.5277 | 1830.74 | 25.99 | 19.36 | 19.47 |
| 60% | 40% | 1200 | 800 | 0.5113 | 1772.88 | 26.01 | 19.29 | 19.42 |
| 50% | 50% | 1000 | 1000 | 0.495 | 1715.74 | 26.01 | 19.21 | 19.37 |
| 40% | 60% | 800 | 1200 | 0.4785 | 1658.42 | 26.03 | 19.14 | 19.33 |
| 30% | 70% | 600 | 1400 | 0.4622 | 1600.02 | 26.07 | 19.05 | 19.27 |
| 20% | 80% | 400 | 1600 | 0.4459 | 1542.52 | 26.11 | 18.96 | 19.21 |
| 10% | 90% | 200 | 1800 | 0.4296 | 1485.21 | 26.21 | 18.85 | 19.13 |
| 0% | 100% | 0 | 2000 | 0.4142 | 1430.93 | 26.24 | 18.71 | 19.02 |

BINARY GAS PURITY ANALYZER

BACKGROUND

Binary gas mixtures are used in a variety of vacuum industrial processing and scientific applications. Typical application areas include semiconductor manufacturing processes, thin-film coating, and aerospace applications. For such applications, it can be beneficial or necessary to monitor the presence or percentage of a particular gas (A) with respect to another particular gas (B) in a gas stream. Some of the processes that benefit from careful monitoring and control of binary gas flow streams include Metal Organic Chemical Vapor Deposition (MOCVD) for the semiconductor manufacturing industry, reactive sputtering for the thin film coating industry, and gas stream purity analyzers for the aerospace industry.

Existing methods of monitoring binary gas compositions include mass spectrometry, Fourier-Transform Infrared Optical Spectrometry (FTIR), speed-of-sound sensors and catalytic sensing. There exists a need for improved binary gas analysis systems and methods.

SUMMARY

Methods and systems for binary gas analysis are provided. Such methods and systems can provide for straightforward, low-cost, and accurate binary gas monitoring using sensing devices that can be easily integrated into existing systems and usable for a broad variety of applications.

A method of analyzing a composition of a binary gas mixture includes, with a species-dependent mass flow meter, sensing a mass flow rate of a binary gas mixture comprising gases of differing gas correction factors and, with a species-independent pressure sensor, sensing a total pressure of the binary gas mixture. The method further includes providing an output representative of a relative concentration of one gas of the binary gas mixture, the relative concentration determined as a function of the sensed mass flow rate and the sensed total pressure.

The species-dependent mass flow meter can be a thermal mass flow meter. The output can be a percentage volumetric flow of the one gas of the binary gas mixture with respect to a total volumetric flow of the binary gas mixture. Alternatively, or in addition, the output can be an alarm indicating the relative concentration of one gas of the binary gas mixture is above or beneath a threshold value.

The function of the sensed mass flow rate and the sensed total pressure can be in accordance with the following:

$$P_T = f_P(Q_a, Q_b, T)$$

$$Q_{MFM} = f_Q(Q_a, Q_b, T)$$

where $Q_a$ is a mass flow of a first gas of the binary gas mixture, $Q_b$ is a mass flow of a second gas of the binary gas mixture, T is a temperature of the gas mixture, $Q_{MFM}$ is the sensed mass flow rate, and $P_T$ is the sensed total pressure. For example, $f_P$ and $f_Q$ can be further defined as follows:

$$P = f_P(Q_a, Q_b, T) = (k1 \cdot Q_a + k2 \cdot Q_b) \cdot T$$

$$Q_{MFM} = f_Q(Q_a, Q_b, T) = k3 \cdot Q_a + k4 \cdot Q_b + k5 \cdot T$$

where k1-k5 are constants. The method can further include determining the constants k1-k5.

The binary gas mixture can be supplied to a chamber, and the method can include maintaining a substantially constant volumetric flow of the binary gas mixture through the chamber, such as with a constant volume pump. The function of the sensed mass flow rate and the sensed total pressure can be in accordance with the following:

$$Q_a = (Q_{MFM} - GCF_b \cdot P_T \cdot S)/(GCF_a - GCF_b); \text{ and}$$

$$Q_b = P_T \cdot S - Q_a.$$

where $Q_a$ is a mass flow of a first gas of the binary gas mixture, $Q_b$ is a mass flow of a second gas of the binary gas mixture, $GCF_a$ is a gas correction factor of the first gas, $GCF_b$ is a gas correction factor of the second gas, $Q_{MFM}$ is the sensed mass flow rate, $P_T$ is the sensed total pressure, and S is a pumping speed of the constant volume pump. The method can further include determining the pumping speed of the constant volume pump S.

Alternatively, a flow restriction can be disposed downstream of the mass flow meter and the function can be in accordance with the following:

$$Q_a = (Q_{MFM} - GCF_b \cdot C_b \cdot \Delta P)/(GCF_a - (GCF_b \cdot C_b/C_a));$$

$$Q_b = C(\Delta P - (Q_a/C_a)); \text{ and}$$

$$\Delta P = (Q_a/C_a) + (Q_b/C_b) = (P_T - P_{vent}).$$

where $Q_a$ is a mass flow of a first gas of the binary gas mixture, $Q_b$ is a mass flow of a second gas of the binary gas mixture, $GCF_a$ is a gas correction factor of the first gas, $GCF_b$ is a gas correction factor of the second gas, $C_a$ is a conductance of the first gas through the flow restriction, $C_b$ is a conductance of the second gas through the flow restriction, $Q_{MFM}$ is the sensed mass flow rate, $P_T$ is the sensed total pressure, and $P_{vent}$ is a pressure external of the construction through which the gas is vented. A substantially constant pressure of the binary gas mixture upstream of the flow restriction can be maintained, or the pressure may be permitted to vary.

The method can further include determining a restriction conductance of each of the gases of the binary gas mixture, determining a gas correction factor of each of the gases of the binary gas mixture, or both.

A system for analyzing a composition of a binary gas mixture includes a species-dependent mass flow meter configured to sense a mass flow rate of a binary gas mixture comprising gases of differing gas correction factors and a species-independent pressure sensor configured to sense a total pressure of the binary gas mixture. The system further includes a controller configured to provide an output representative of a relative concentration of at least one gas of the binary gas mixture, the relative concentration determined as a function of the sensed total pressure and the sensed mass flow rate.

The species-dependent mass flow meter can be a thermal mass flow meter. The system can further include a temperature sensor configured to sense a temperature of the binary gas mixture. The function of the sensed total pressure and the sensed mass flow rate can be in accordance with the following:

$$P_T = f_P(Q_a, Q_b, T)$$

$$Q_{MFM} = f_Q(Q_a, Q_b, T)$$

where $Q_a$ is a mass flow of a first gas of the binary gas mixture, $Q_b$ is a mass flow of a second gas of the binary gas mixture, T is a temperature of the gas mixture, $Q_{MFM}$ is the sensed mass flow rate, and $P_T$ is the sensed total pressure. For example, $f_P$ and $f_Q$ can be further defined as follows:

$$P_T = f_P(Q_a, Q_b) = (k1 \cdot Q_a + k2 \cdot Q_b)T$$

$$Q_{MFM} = f_Q(Q_a, Q_b, T) = k3 \cdot Q_a + k4 \cdot Q_b + k5 \cdot T$$

where k1-k5 are constants.

The system can further include a chamber and an output pump. The output pump can be configured to evacuate the binary gas mixture from the chamber, for example, to maintain a constant volumetric flow of the binary gas mixture through the chamber. The function can be in accordance with the following:

$$Q_a = (Q_{MFM} - GCF_b \cdot P_T \cdot S)/(GCF_a - GCF_b); \text{ and}$$

$$Q_b = P_T \cdot S - Q_a.$$

where $Q_a$ is a mass flow of a first gas of the binary gas mixture, $Q_b$ is a mass flow of a second gas of the binary gas mixture, $GCF_a$ is a gas correction factor of the first gas, $GCF_b$ is a gas correction factor of the second gas, $Q_{MFM}$ is the sensed mass flow rate, $P_T$ is the sensed total pressure, and S is a pumping speed of the output pump.

Alternatively, the system can further include a flow restriction disposed downstream of the mass flow meter. The function can be in accordance with the following:

$$Q_a = (Q_{MFM} - GCF_b \cdot C_b \cdot \Delta P)/(GCF_a - (GCF_b \cdot C_b/C_a));$$

$$Q_b = C(\Delta P - (Q_a/C_a)); \text{ and}$$

$$\Delta P = (Q_a/C_a) + (Q_b/C_b) = (P_T - P_{vent}).$$

where $Q_a$ is a mass flow of a first gas of the binary gas mixture, $Q_b$ is a mass flow of a second gas of the binary gas mixture, $GCF_a$ is a gas correction factor of the first gas, $GCF_b$ is a gas correction factor of the second gas, $C_a$ is a conductance of the first gas through the flow restriction, $C_b$ is a conductance of the second gas through the flow restriction, $Q_{MFM}$ is the sensed mass flow rate, $P_T$ is the sensed total pressure, and $P_{vent}$ is a pressure external of the outlet to which the gas is vented.

The mass flow meter can be a mass flow controller configured to supply the binary gas mixture to a volume. For example, the binary gas mixture can be supplied to the volume at a rate that maintains a constant pressure of gases within the volume, and/or a control valve can be included to maintain a constant pressure within the volume.

The output can be a percentage volumetric flow of the one gas of the binary gas mixture with respect to a total volumetric flow of the binary gas mixture. Alternatively, or in addition, the output can be an alarm indicating the relative concentration of one gas of the binary gas mixture is above or beneath a threshold value.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
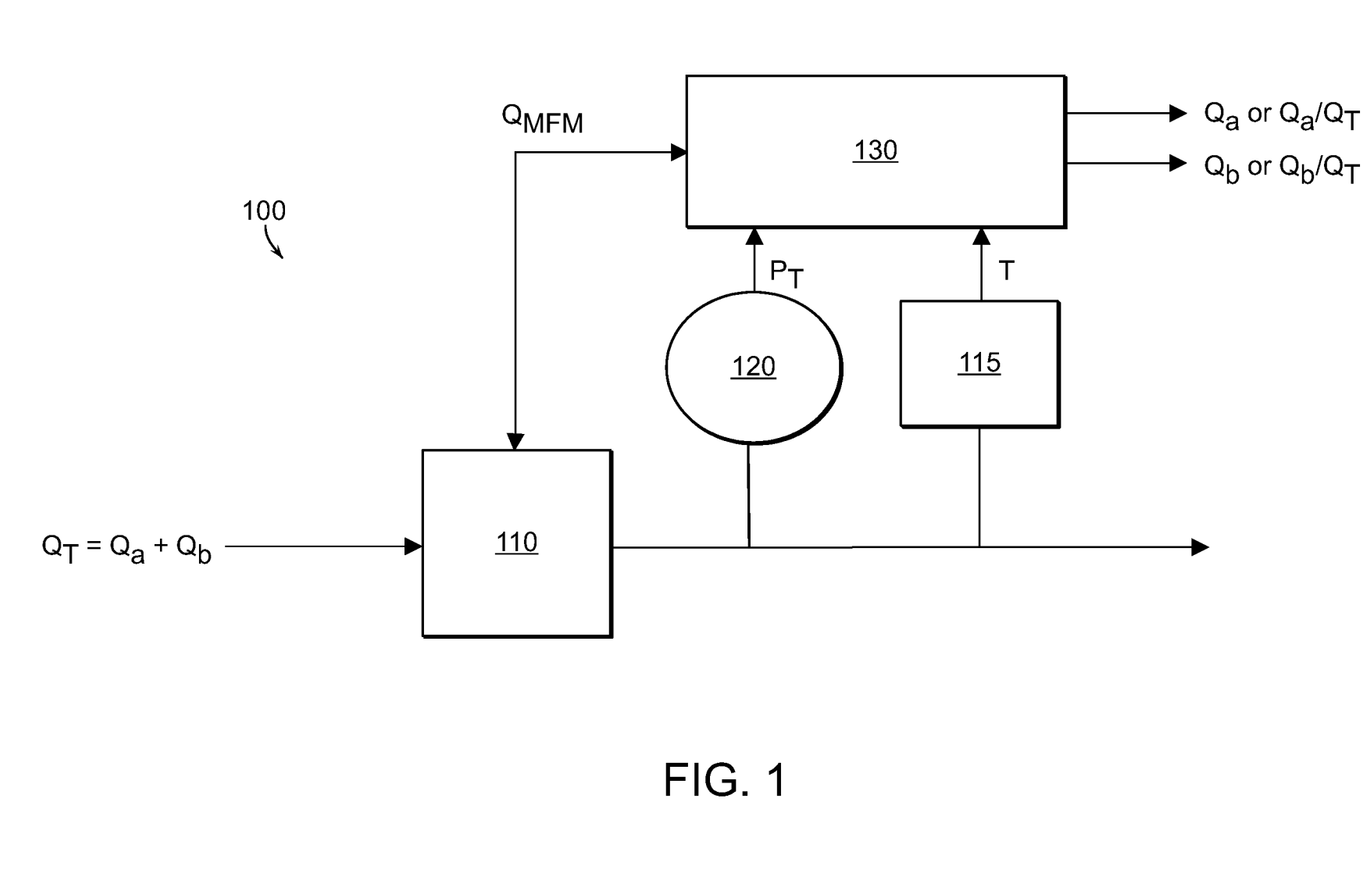
FIG. 1 is a schematic of a binary gas analyzer, alternatively referred to as a binary gas detector.

An example method and system of detecting a composition of a binary gas mixture is shown in FIG. 1. A binary gas analyzer 100 includes a species-dependent mass flow reader 110, such as a thermal mass flow meter, and a species-independent pressure sensor 120. As a flow of a binary gas mixture ($Q_a$ and $Q_b$) is provided to the system, a mass flow rate of the mixture ($Q_{MFM}$) is sensed by the mass flow reader 110, and a total pressure ($P_T$) of the mixture is sensed by the pressure sensor 120. The pressure sensor 120 is a species-independent sensor, such as a capacitance manometer or a capacitance diaphragm gauge. A controller 130 is configured to provide an output representative of a relative concentration of at least one gas of the binary gas mixture (e.g., $Q_a$, $Q_b$, $Q_a/Q_T$, $Q_b/Q_T$, or any combination thereof).

Provided that the mass flow gas correction factors (GCFs) of the gases of the mixture differ, a concentration of one or both of the gases can be determined as a function of the sensed total pressure and the sensed mass flow rate. Readings provided by a thermal mass flow meter are species-dependent as such readings depend upon specific heat and density of the gas being measured. A GCF accounts for the density and specific heat of a particular gas, and GCFs are used in conjunction with thermal mass flow readers such that accurate mass flow readings for the particular gas can be provided by the reader.

The following discussion is provided with respect to thermal mass flow meters for illustration purposes; however, it should be understood that other types of species-dependent flow meters can be included in the systems and methods described herein. In general, mass flow meters that provide different flow readings for differing gas concentrations where total flow remains the same can be included in the systems and methods described herein. For example, Corolis mass flow meters or ultrasonic mass flow verifiers can be included.

Typically, thermal mass flow readers are calibrated to nitrogen. A GCF for such a reader can be defined as follows:

$$GCF = \frac{0.3106 \times \text{Molecular Structure Correction Factor}}{\text{Density at } STP\left(\frac{\text{mgms}}{\text{liter}}\right) \times \text{Specific Heat}\left(\frac{\text{cal}}{\text{gm}^\circ \text{C.}}\right)} \quad (1)$$

The value 0.3106 represents the product of the density of nitrogen and the specific heat of nitrogen. The Molecular Structure Correction Factor can be 1.030 for monatomic gases, 1.000 for diatomic gases, 0.941 for triatomic gases, and 0.880 for polyatomic gases. The equation for determining a GCF shown above is provided as an example. Thermal mass flow readers may be calibrated to gases other than nitrogen. As used herein, the term "gas correction factor" or "GCF" means a value that accounts for density and specific heat of a particular gas with respect to a reading by a thermal mass flow reader.

With a species-dependent reading provided by a thermal mass flow reader and a species-independent reading provided by a pressure sensor, a concentration of each of the gases in a binary gas mixture can be determined. In a generalized form:

$$P_T = f_P(Q_a, Q_b, T) \quad (2)$$

$$Q_{MFM} = f_Q(Q_a, Q_b, T) \quad (3)$$

The function $f_P$ is a function that relates the flow of gas A ($Q_a$), the flow of gas B ($Q_b$) and gas temperature (T) to the total pressure ($P_T$) measured by the pressure sensor. The function $f_Q$ is a function that relates the flow of gas A ($Q_a$), the flow of gas B ($Q_b$) and gas temperature (T) to the reported flow ($Q_{MFM}$) measured by the thermal mass flow meter. Values for $P_T$, $Q_{MF}$M, and T can be measured by corresponding sensors or transducers. Accordingly, values of $Q_a$ and $Q_b$ can be obtained by solving Eqns. 2 and 3 using the measured values of $P_T$, $Q_{MFM}$, and T.

The functions $f_P$ and $f_Q$ can vary depending upon whether the system is one in which a substantially constant pressure is maintained, one in which a substantially constant volumetric flow is maintained, or one in which pressure and volumetric flow are permitted to vary. The functions $f_P$ and $f_Q$ can also vary depending upon whether the system is one in which a constant temperature is maintained.

For example, the functions $f_P$ and $f_Q$ can be defined as follows, where k1, k2, k3, k4, and k5 are constants:

$$P_T = f_P(Q_a, Q_b, T) = (k1 \cdot Q_a + k2 \cdot Q_b) \cdot T \quad (2.1)$$

$$Q_{MFM} = f_Q(Q_a, Q_b, T) = k3 \cdot Q_a + k4 \cdot Q_b + k5 \cdot T \quad (3.1)$$

As illustrated in FIG. 1, the system can include an optional temperature detector 115 configured to provide a temperature reading to the controller 130. The constants k1-k5 can be determined empirically for a system through application of a multivariable regression method to experimental data. For example, experimental data can be obtained by varying $Q_a$, $Q_b$, and T, and a multivariable regression method can be used to determine the constants for functions $f_P$ and $f_Q$ with measured values for $P_T$ and $Q_{MFM}$. Multivariable regression methods are generally known in the art. Equations 2.1 and 3.1 are provided as example functions if a linear relationship among multiple variables is selected (e.g., a first-order Taylor expansion approximation). Higher-ordered functions can alternatively be selected and used for defining the functions $f_P$ and $f_Q$.

While temperature can be permitted to vary in some systems, for many applications, temperature remains constant. As such, the functions $f_P$ and $f_Q$ can be defined without a temperature value (T) as a temperature effect can be either ignored or embedded into other constants.

Figure 2:
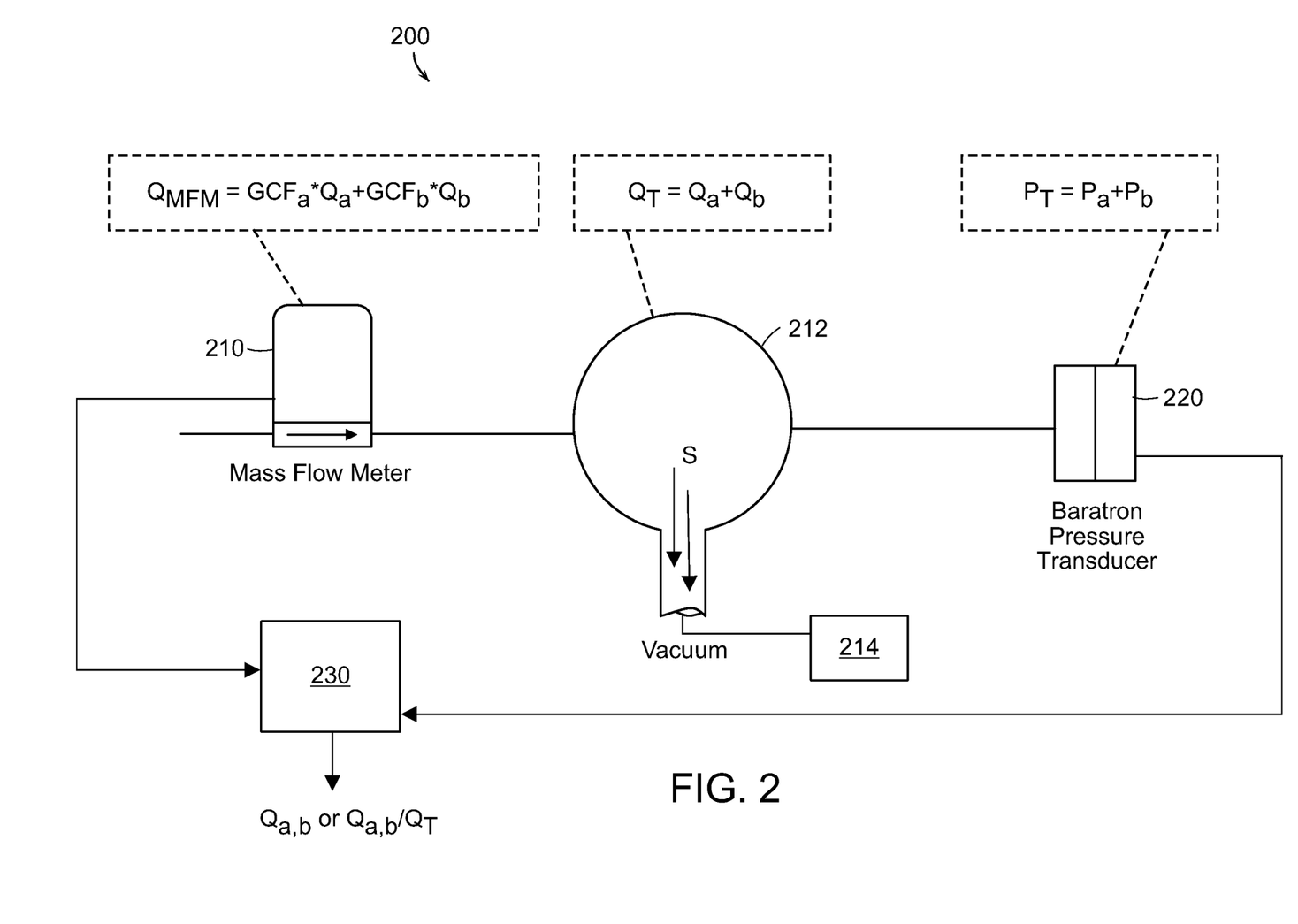
FIG. 2 is a schematic of a binary gas analyzer as applied in a constant volume system.

As illustrated in FIG. 2, a system 200 can include a chamber 212, such as a vacuum chamber. A substantially constant volumetric flow of the binary gas mixture through the chamber 212 can be maintained. For example, the chamber 212 can be evacuated by a constant volume pump 214 that can provide for a constant pumping speed for all gas species. The system 200 further includes a thermal mass flow reader 210 and a pressure sensor 220 (e.g., a Baratron® pressure transducer) that monitors pressure inside the process chamber 212. Pressure within the chamber is a result of dynamic equilibrium between an incoming flow of gas ($Q_T$) and a volumetric speed (S) of the pump 214. With a flow rate ($Q_{MFM}$) reported by the thermal mass flow reader and a total pressure ($P_T$) reported by the pressure sensor 220, the flow rates for each individual gas in the flow stream ($Q_a$, $Q_b$) can be determined, provided that gas correction factors of each gas differ from one another (i.e., $GCF_a \neq GCF_b$).

In the equation derivations that follow, it is assumed that the pumping speed (S) is pressure-independent and gas-species-independent. It is also assumed that the gas temperature (T) is constant.

The pumping speed can be a known value or can be determined by, for example, pumping pure nitrogen through the system 200. Where the thermal mass flow reader 210 is initially calibrated for nitrogen ($N_2$):

$$Q_{MFM} = Q_{N2} \quad (4)$$

$$P_T = \frac{Q_{N2}}{S} \quad (5)$$

A value for the volumetric speed (S) of the pump 214 can thereby be determined based on readings obtained by the thermal mass flow meter 210 and the pressure sensor 220 while pure nitrogen is flowing through the system. Specifically, and with $P_{CDG}$ indicating pressure obtained by the pressure sensor 220 (for example, a capacitance diaphragm gauge):

$$S = \frac{Q_{N2}}{P_T} = \frac{Q_{MFM}}{P_{CDG}} \quad (6)$$

The GCF of each gas in a binary gas mixture can be of a known value or can be determined by independently introducing each gas to the system. In particular, while flowing sample gas A through the system:

$$Q_{MFM} = GCF_a \cdot Q_a \quad (7)$$

$$P_T = \frac{Q_a}{S} \quad (8)$$

With a known value of the volumetric speed (S) of the pump 214 and measurements obtained for $Q_{MFM}$ and $P_T$, $GCF_a$ can be determined. Specifically:

$$GCF_a = \frac{Q_{MFM}}{Q_a} = \frac{Q_{MFM}}{P_{CDG} \cdot S} \quad (9)$$

Similarly, while flowing pure sample gas B through the system:

$$Q_{MFM} = GCF_b \cdot Q_b \quad (10)$$

$$P_T = \frac{Q_b}{S} \quad (11)$$

With a known value of the volumetric speed (S) of the pump 214 and measurements obtained for $Q_{MFM}$ and $P_T$, $GCF_b$ can be determined. Specifically:

$$GCF_b = \frac{Q_{MFM}}{Q_b} = \frac{Q_{MFM}}{P_{CDG} \cdot S} \quad (12)$$

With a mixed flow provided to the system 200, the following is provided:

$$Q_a + Q_b = P_T \cdot S \quad (13)$$

$$GCF_a \cdot Q_a + GCF_b \cdot Q_b = Q_{MFM} \quad (14)$$

Rearranging terms in Eqn. 13 provides:

$$Q_b = (P_T \cdot S) - Q_a \quad (15)$$

Substituting for $Q_b$ in Eqn. 14 provides:

$$GCF_a \cdot Q_a + GCF_b \cdot [(P_T \cdot S) - Q_a] = Q_{MFM} \quad (16)$$

Rearranging terms of Eqn. 16 for the determination of a flow rate of $Q_a$ provides:

$$GCF_a \cdot Q_a + GCF_b \cdot P_T \cdot S - GCF_b \cdot Q_a = Q_{MFM} \quad (16.1)$$

$$GCF_a \cdot Q_a - GCF_a \cdot Q_a = Q_{MFM} - GCF_b \cdot P_T \cdot S \quad (16.2)$$

$$(GCF_a - GCF_b)Q_a = Q_{MFM} - GCF_b \cdot P_T \cdot S \quad (16.3)$$

$$Q_a = \frac{Q_{MFM} - GCF_b \cdot P_T \cdot S}{GCF_a - GCF_b} \quad (17)$$

Thus, a flow rate of one of the gases of the binary mixture ($Q_a$) can be determined using Eqn. 17 based on total pressure $P_T$, as detected by a species-independent pressure sensor, and a mass flow rate $Q_{MFM}$, as measured by a thermal mass flow meter. Upon obtaining a value for the mass flow of gas A ($Q_a$), the mass flow of gas B ($Q_b$) can be determined with Eqn. 15. In the above-described method, the mass flow meter functions as a species-dependent sensor, and, thus, where $GCF_a \neq GCF_b$, a composition of the binary gas mixture can be derived. Accuracy and minimum detectable concentrations can improve where there is a greater difference in $GCF_a$ and $GCF_b$.

As noted above, a constant temperature system is presumed in the equation derivations shown by Eqns. 4-17. It can be shown that Eqn. 2.1 can encompass Eqn. 13, which, rearranged, can be provided as:

$$P_T = \frac{1}{S} \cdot Q_a + \frac{1}{S} \cdot Q_b \quad (13.1)$$

In comparison with Eqn. 2.1, repeated here:

$$P_T = f_P(Q_a, Q_b, T) = (k1 \cdot Q_a + k2 \cdot Q_b) \cdot T \quad (2.1)$$

it can be seen that:

$$\frac{1}{S} = k1 \cdot T \quad (13.2)$$

$$\frac{1}{S} = k2 \cdot T \quad (13.3)$$

With a constant temperature, both sides of Eqns. 13.2 and 13.3 can thereby be constant values. As such, it can be shown that $f_P$ can be defined in multiple ways for a given system.

A controller 230 is included in the system 200 to perform the operations described above and provide an output representative of a relative concentration of at least one gas in the binary gas mixture. For example, a controller 130, 230 can be configured to output $Q_a$ and $Q_b$, which are indicative of the relative concentrations of gases A, B. Alternatively, or in addition, a ratiometric output can be provided, such as, for example, $Q_a/Q_T$ and $Q_b/Q_T$, a molar ratio of the gases in the mixture, a percentage volume of one or both of the gases in the mixture, a relative partial pressure of one or both of the gases in the mixture, or any combination thereof, each of which can also provide for an output indicative of a relative concentration of at least one gas in the binary gas mixture. The controller can be configured to provide for an alert or an alarm if a detected concentration of one of the gases exceeds or falls beneath a threshold value. Such an alarm output can be useful for gas-purity monitoring applications.

Figure 3:
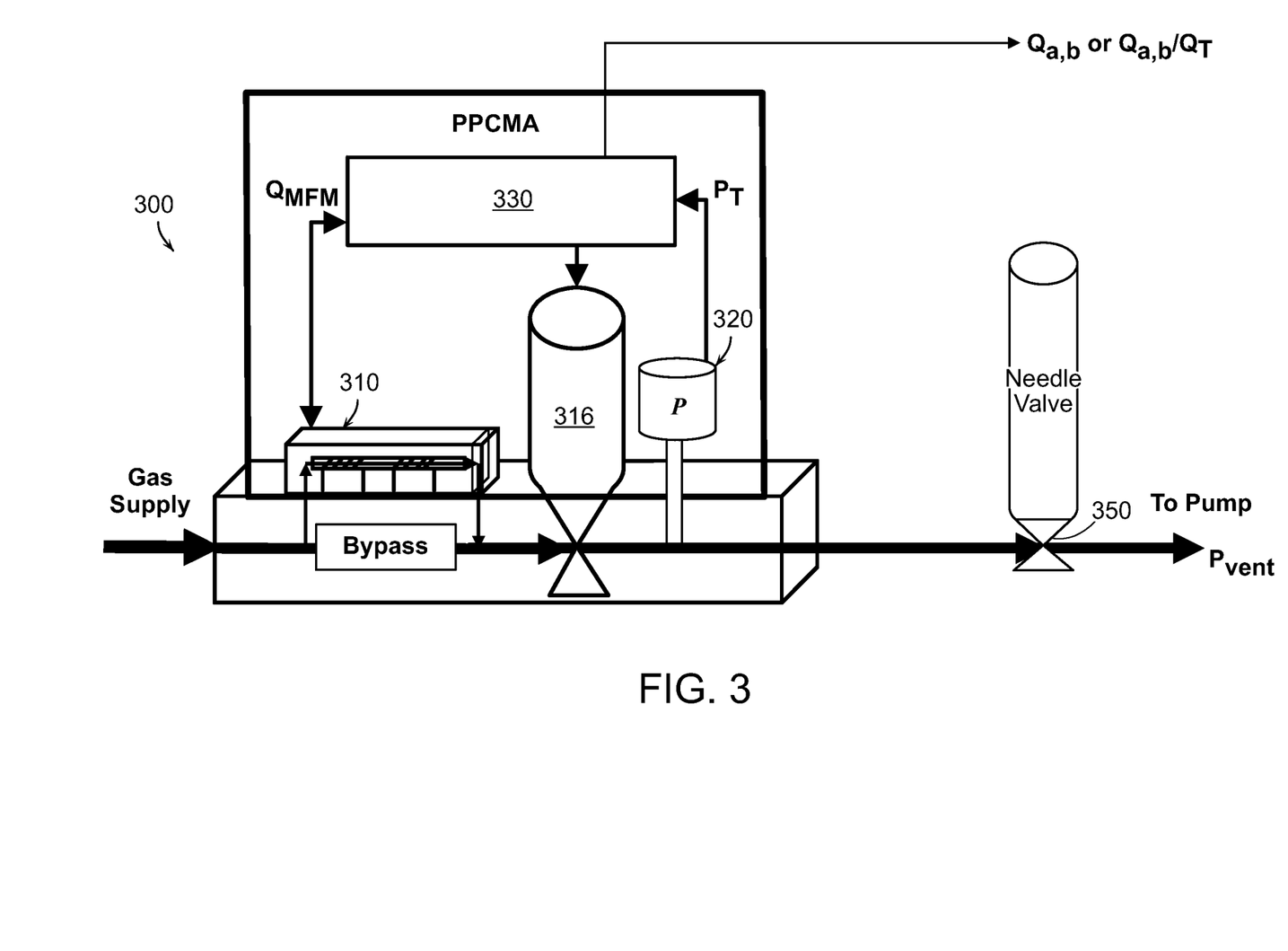
FIG. 3 is a schematic of a binary gas analyzer as applied in a constant pressure system.

An example of a constant-pressure system is shown in FIG. 3. The system 300 includes a thermal mass flow reader 310, a control valve 316, a pressure sensor 320, and a flow restriction 350, such as provided by a needle valve. The system further includes a controller 330 configured to provide an output representative of a relative concentration of at least one gas of a binary gas mixture flowing through the system (e.g., $Q_a$, $Q_b$, a ratiometric output, a percentage volume, or any combination thereof, as described above with respect to controllers 130, 230). In the system 300, gas flow is vented through the flow restriction 350, with $P_{vent}$ being an external pressure. For example, a system can vent to atmosphere or ambient pressure. Alternatively, $P_{vent}$ can be dependent upon a downstream pump.

As illustrated, the mass flow reader 310 is disposed upstream of the control valve 316, but can alternatively be placed downstream of the control valve 316. A downstream pressure of the pressure controller with mass flow meter (PPCMA) can be regulated or controlled to a predetermined pressure setpoint while the flow can be permitted to vary.

A restriction conductance ($C_g$) of a gas (g) with respect to the flow restriction 350 is provided by:

$$C_g = \frac{Q_g}{\Delta P} \quad (18)$$

A pressure drop across the flow restriction ($\Delta P$) is defined as a difference between the total pressure ($P_T$, as provided by the pressure sensor 320) upstream of the constriction and the vent pressure ($P_{vent}$), in particular, $\Delta P = P_T - P_{vent}$.

The pressure drop across the restriction can be given by:

$$\Delta P = \frac{Q_a}{C_a} + \frac{Q_b}{C_b} \quad (19)$$

A reading provided by the thermal mass flow reader 310 is in accordance with Eqn. 14, repeated here:

$$GCF_a \cdot Q_a + GCF_b \cdot Q_b = Q_{MFM} \quad (14)$$

Combining Eqns. 14 and 19 and rearranging terms provides for determination of the flow of each gas ($Q_a$, $Q_b$) as follows:

$$Q_a = \frac{Q_{MFM} - GCF_b \cdot C_b \cdot \Delta P}{GCF_a - (GCF_b \cdot C_b / C_a)} \quad (20)$$

$$Q_b = C_b \left[ \Delta P - \frac{Q_a}{C_a} \right] \quad (21)$$

In a constant pressure system with a constant vent pressure, $\Delta P$ can be a constant value. Where a vacuum is applied, $\Delta P$ will generally be equal to a total pressure of the system ($P_T$).

The restriction conductance of each gas ($C_a$, $C_b$) in the mixture can be of a known value or can be determined by independently introducing each gas to the system and, with measurements provided by the thermal mass flow meter and the pressure sensor, using Eqn. 18 to obtain a value for the conductance. The system shown in FIG. 3, as well as that described below with FIG. 4, does not rely solely on $GCF_a \neq GCF_b$ as differences in $C_a$ and $C_b$ also contribute to the determination of $Q_a$ and $Q_b$.

It can also be shown that an equation similar to Eqn. 2.1 can encompass Eqn. 19. Where $\Delta P = P_T - P_{vent}$, Eqn. 19 can be re-expressed as follows:

$$P_T - P_{vent} = \frac{Q_a}{C_a} + \frac{Q_b}{C_b} \quad (19.1)$$

$$P_T = \frac{Q_a}{C_a} + \frac{Q_b}{C_b} + P_{vent} \quad (19.2)$$

In comparison with Eqn. 2.1, repeated here:

$$P_T = f_P(Q_a, Q_b, T) = (k1 \cdot Q_a + k2 \cdot Q_b) \cdot T \quad (2.1)$$

it can generally be seen that:

$$\frac{1}{C_a} = k1 \cdot T \quad (19.3)$$

$$\frac{1}{C_a} = k2 \cdot T \quad (19.4)$$

Note, however, that $P_{vent}$ is unaccounted as Eqn. 2.1 is but one example of Eqn. 2. To account for $P_{vent}$ another example function for Eqn. 2 and a variation of Eqn. 2.1 can be defined as follows:

$$P_T = f_P(Q_a, Q_b, T) = (k1 \cdot Q_a + k2 \cdot Q_b + k0) \cdot T \quad (2.2)$$

Thus, it can be seen that:

$$\frac{1}{C_a} = k1 \cdot T \quad (19.3)$$

$$\frac{1}{C_b} = k2 \cdot T \quad (19.4)$$

$$P_{vent} = k0 \cdot T \quad (19.5)$$

With a constant temperature, both sides of each of Eqns. 19.3-19.5 can thereby be constant values. As such, it can be shown that $f_P$ can be defined in multiple ways for a given system.

Figure 4:
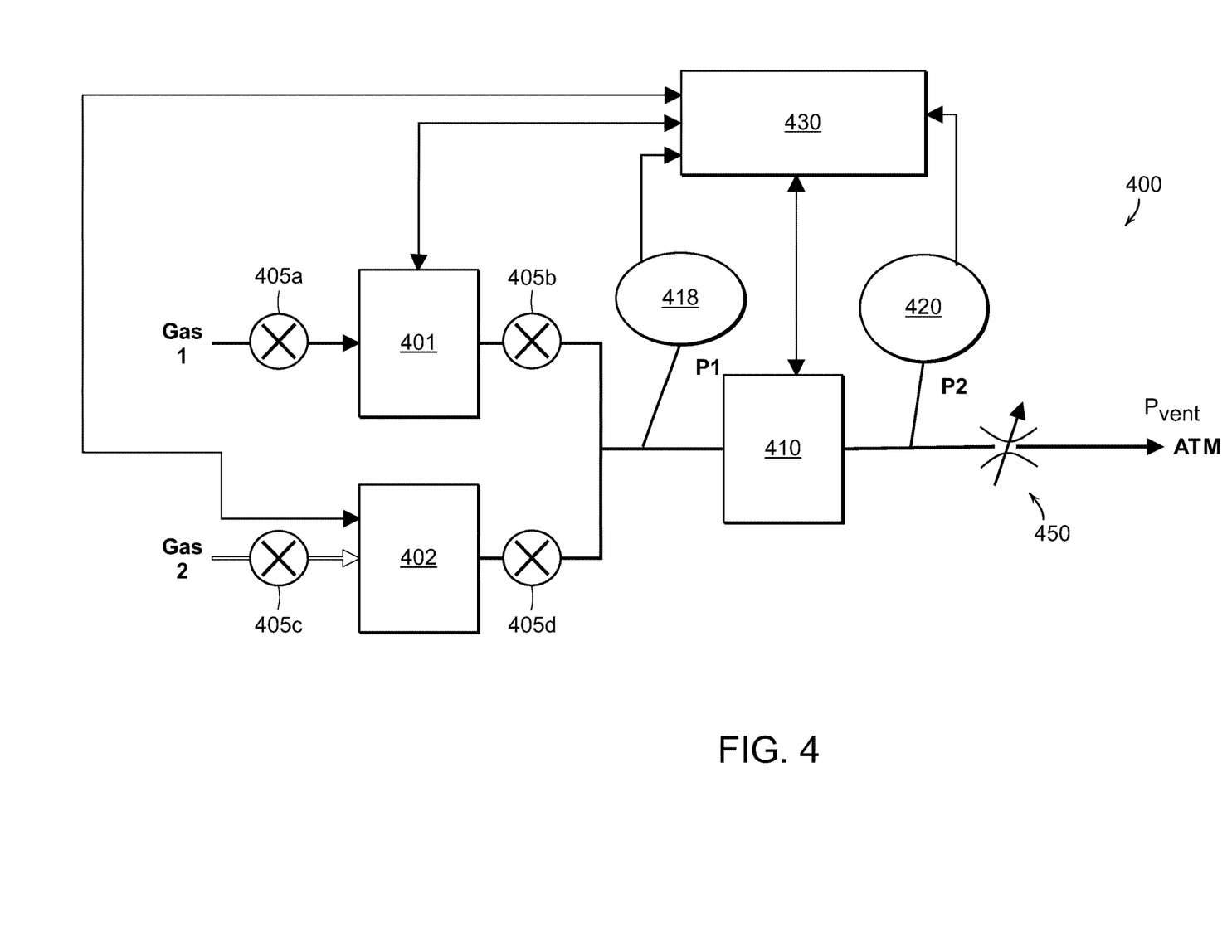
FIG. 4 is a schematic of a binary gas analyzer as applied in a system in which volume and pressure can be permitted to vary and representing a test setup with which experimentation was performed.

A system in which both pressure and volumetric flow can be permitted to vary is shown in FIG. 4. The schematic shown in FIG. 4 also represents a test setup of validating a prototype binary gas sensor and includes additional elements beyond those required for a binary gas analyzer (e.g., mass flow controllers, associated valves, additional pressure sensor). Test results are described further in Examples 1 and 2, below.

The system 400 includes a mass flow controller 401 and associated valves 405a, 405b for a first gas (Gas 1) and a mass flow controller 402 and associated values 405c, 405d for a second gas (Gas 2). A first pressure sensor 418 is disposed upstream of a mass flow meter 410, and a second pressure sensor 420 is disposed downstream of the mass flow meter 410. The first pressure sensor 418 is optional and is shown in FIG. 4 as it was included in the experimental setup described in Example 1. A flow restriction 450 vents to atmosphere (ATM). The system can further include a controller 430 to receive readings from the pressure sensors 418, 420, the mass flow meter 410, and, optionally, the mass flow controllers 401, 402.

The controller 430 can be configured to perform any of the operations described above and provide an output representative of a relative concentration of at least one gas of a binary gas mixture flowing through the system (e.g., $Q_a$, $Q_b$, a ratiometric output, a percentage volume, or any combination thereof, as described above with respect to controllers 130, 230, 330).

Any of systems 100-400 can be calibrated by introducing each gas independently into the system. Using pressure and flow measurements provided by the species-independent pressure sensor 120, 220, 320, 420 and the thermal mass flow meter 110, 210, 310, 410, any of function constants (e.g., k1-k5), gas correction factors, gas restriction conductances, and pumping speed can be determined, as described above.

Optionally, the controllers 130, 230, 330, 430 can control operation of components of their respective systems, such as, for example, valves (e.g., valves 316, 405a-d), and mass flow controllers (e.g., 401, 402, or, where a mass flow meter is a mass flow controller, 110, 210, 310, 410).

Routine calibration procedures can be performed to discipline the sensors against each other and to eliminate reliance on out-of-the-box accuracy specifications. For example, whereas an out-of-the-box accuracy of a mass flow meter can be 1% full scale (FS), repeatability can be better than 0.1% of the measurement provided by the MFM with calibration. Routine accuracy calibrations can be performed to achieve lowest possible detection limits.

Examples of suitable thermal mass flow meters include G-series and P-series mass flow controllers/meters (MKS Instruments, Andover, MA). Examples of suitable mass flow controllers include C-series, G-series, and P-series mass flow controllers (MKS Instruments, Andover, MA).

Species-independent pressure sensors can be capacitance diaphragm gauges or other types of capacitance manometers. Alternatively, the species-independent pressure sensor can be a piezoresistive diaphragm (PRD) gauge, a fiber-optic diaphragm deflection gauge, or a fiber Bragg grating (FBR) sensor. Examples of suitable pressure sensors include Baratron® pressure transducers (MKS Instruments, Andover, MA). In general, pressure sensors that measure deflection of a membrane and provide for force/unit area measurements can be suitable species-independent pressure sensors.

Systems and methods of the present invention can provide for several advantages over traditional methods of analyzing the composition of a gas stream. Traditional methods of monitoring gas compositions include mass spectrometry, Fourier-Transform Infrared Optical Spectrometry (FTIR), catalytic sensing, and speed-of-sound sensing. Mass spectrometry can provide for high specificity but is not reliable in typical industrial manufacturing environments. FTIR cannot detect the absorbance of noble gases (i.e., it cannot be used for gases that do not absorb infrared light). Catalytic sensors typically merely provide visual outputs and are often not adequately sensitive for several applications. Speed-of-sound sensors are expensive and are often incompatible with reactive precursors.

In contrast, systems and methods of the present invention can be integrated into several environments, including both sub-atmospheric and above-atmospheric pressure regimes. The sensors included in the binary gas analyzers described are generally low-cost, readily available, rugged for use in manufacturing and production environments, and accurate for sensing across a broad range of pressure regimes (e.g., from approximately 2 Torr in the sub-atmospheric pressure regime and up to approximately 700 psi). The methods and systems described can provided for quantitative measurements, which cannot be achieved with qualitative outputs provided by, for example, catalytic sensors. The methods and systems described herein can be used for binary gas detection, binary gas analysis, and purity checking in gas streams. The systems and methods described can also be used to monitor for the presence of trace water vapor in pure gas streams, which can be useful for the following industrial applications: lyophilization (end point detection), power transformers, bulk gas (facility gas), air-conditioning, refrigeration, and fiberoptic fabrication.

The methods and systems described herein can be used with out-of-the-box equipment specifications; however, calibration can provide for significantly improved output measurements, particularly with respect to binary gas streams comprising gases of similar GCFs. Calibration of the system for gas-dependent parameters (e.g., GCF, C) can provide for high repeatability and advantageously avoid inaccuracies resulting from dependence on out-of-the-box specifications.

EXEMPLIFICATION

Example 1. Nitrogen and Oxygen

Figure 5:
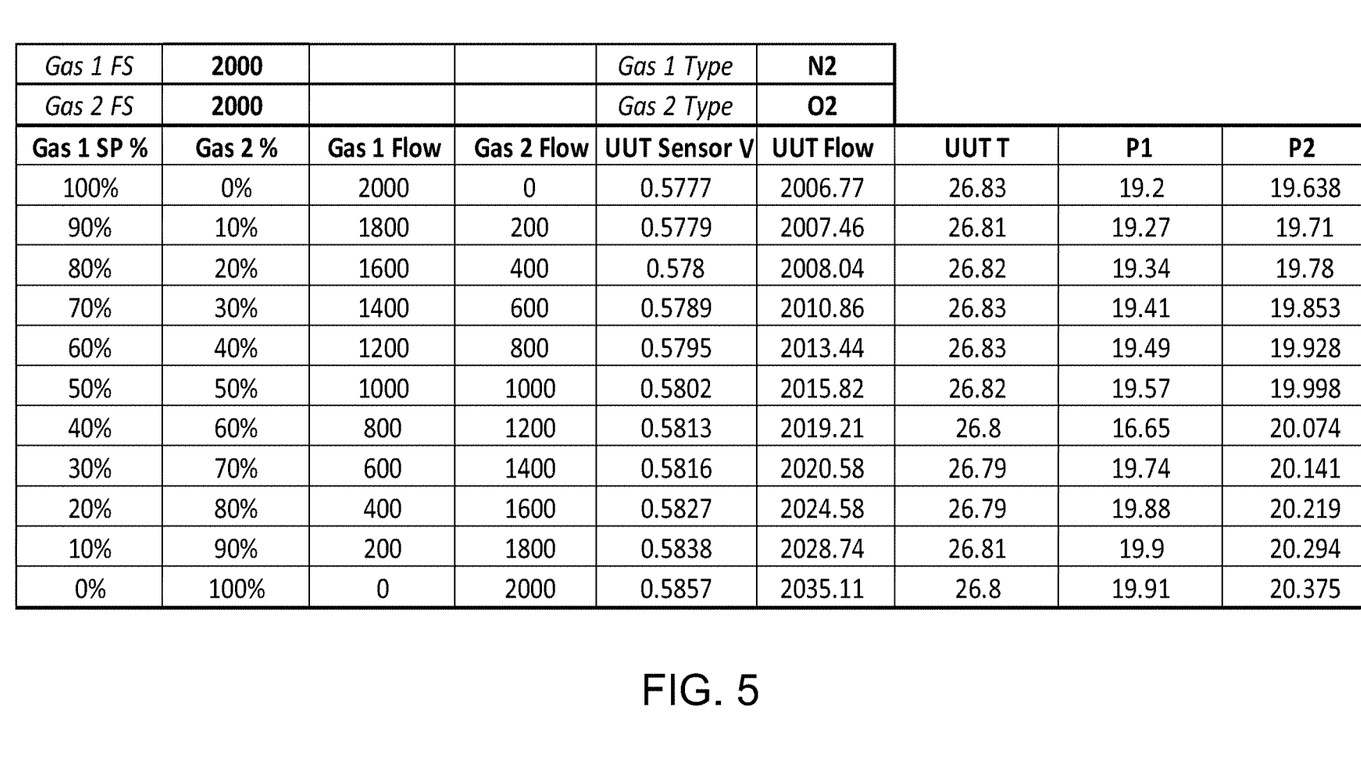
FIG. 5 is a table of test results obtained from the analyzer of FIG. 4 with mixtures of nitrogen and oxygen gases.
Figure 6:
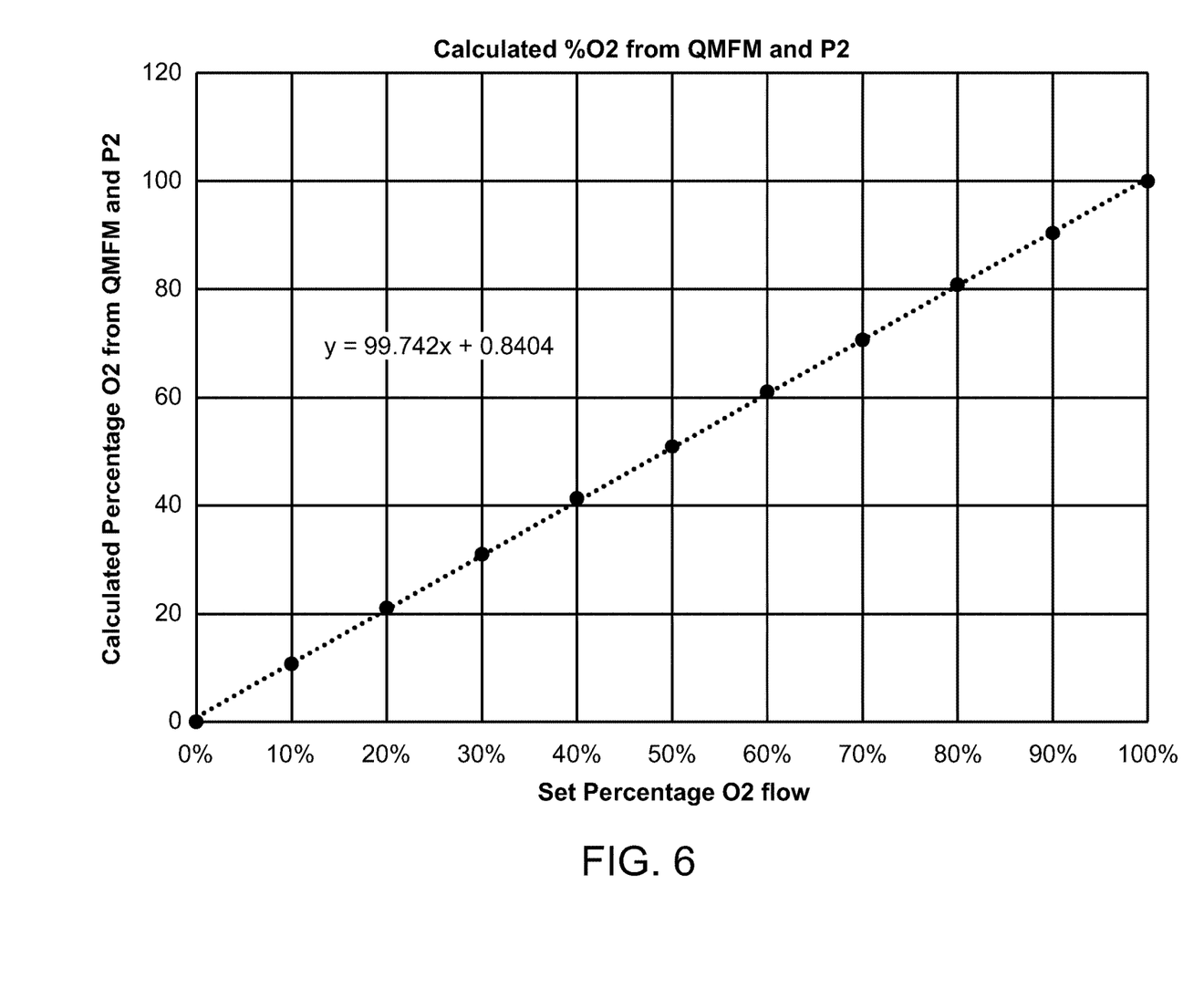
FIG. 6 is a graph of output measurements obtained from the experimental data shown in FIG. 5

With a prototype setup as shown in FIG. 4, binary gas mixtures of nitrogen ($N_2$) and oxygen ($O_2$) were tested, the results of which are shown in FIGS. 5 and 6.

The experimental equipment included two standard liters per minute (SLM) mass flow controllers (MFCs) that were calibrated directly to the primary standard for each gas and gas sources with 40 psia pressure. The setup further included two SLM mass flow meters (MFMs) that were calibrated directly to the primary standard for each gas, an ATM exhaust needle valve set for +5 psig differential at 2 SLM $N_2$ flow, and two 1KT 690 pressure STDs (Baratron®, MKS Instruments). Measurements of pressure are provided in psig, and measurements of flow are provided in sccm.

A calibration procedure was performed to determine species-dependent coefficients. The calibration procedure included: 1) calibrating the MFM with pure Gas A (also referred to as Gas 1) to obtain $GCF_a$; 2) calibrating conductance with pure Gas A to obtain $C_a$; 3) calibrating the MFM with pure Gas B (also referred to as Gas 2) to obtain $GCF_b$; and, 4) calibrating conductance with pure Gas B to obtain $C_b$. The obtained calibration data is shown below in Table 1.

TABLE 1

Calibration Data for Nitrogen and Oxygen

| Restriction Conductances | |
|---|---|
| $C_{N2}$ | 396.9829297 |
| $C_{O2}$ | 346.3203463 |
| Gas Correction Factors | |
| $GCF_{N2}$ | 1.003385 |
| $GCF_{O2}$ | 1.017555 |

Measurements of $Q_{MFM}$ and $P_T$ (also referred to as P2 in FIG. 4) were obtained and used to calculate $Q_a$ ($Q_{N2}$) and $Q_b$ ($Q_{O2}$) according to Eqns. 20 and 21. The obtained measurements are shown in FIG. 5, the calculated values for $Q_{N2}$ are shown below in Table 2, and a plot of the results is shown in FIG. 6. In FIG. 5, the term "UUT" (Unit Under Test) refers to the mass flow meter of the setup.

TABLE 2

Binary Gas Analysis Results for Nitrogen and Oxygen

| $Q_{N2}$ | $Q_{N2}$ (%) |
|---|---|
| 1999.924601 | 100 |
| 1786.578612 | 89 |
| 1578.373782 | 79 |
| 1380.392494 | 69 |
| 1174.244818 | 59 |
| 981.5983033 | 49 |
| 779.4058975 | 39 |
| 587.167356 | 29 |
| 384.1555456 | 19 |
| 191.6646136 | 10 |
| 1.03344E−06 | 0 |

The percentage concentration accuracies remained within 1% throughout the entire tested range. Adequate detection limits were achieved, even though there was not a large difference in GCF values between $N_2$ and $O_2$ (i.e., about 1%).

Example 2. Helium and Nitrogen

Figure 7:
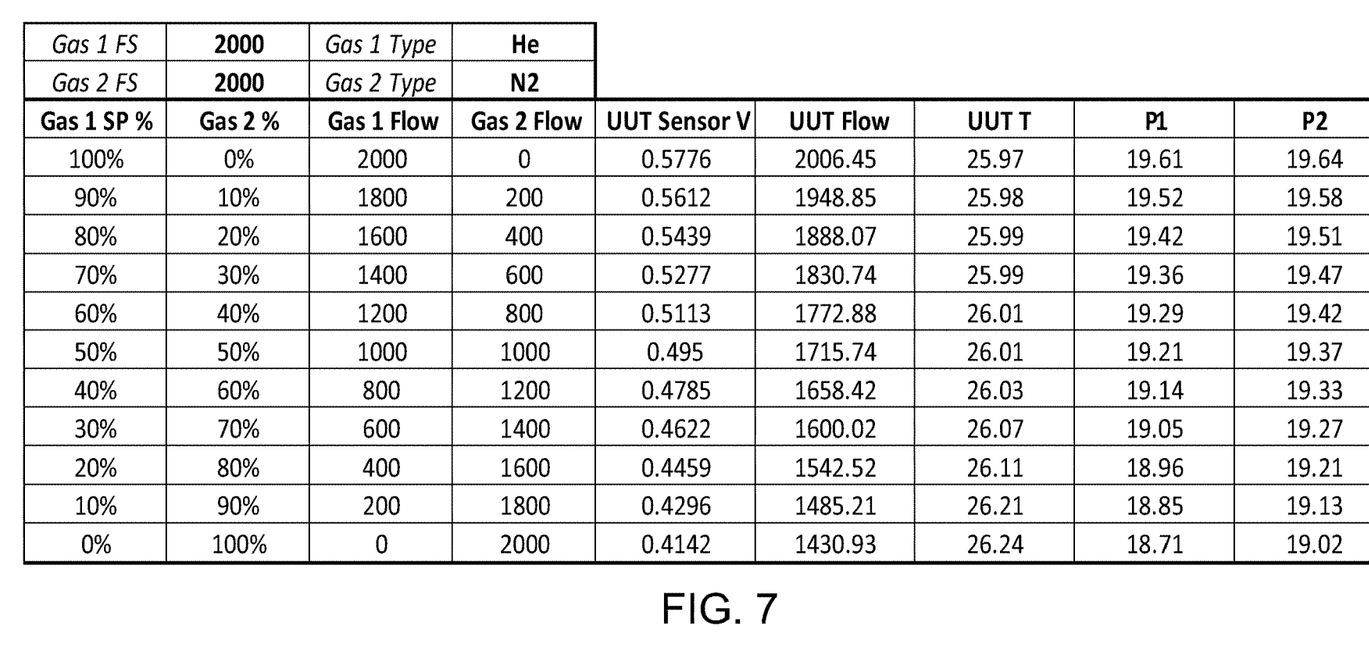
FIG. 7 is a table of test results obtained from the analyzer of FIG. 4 with mixtures of helium and nitrogen gases.
Figure 8:
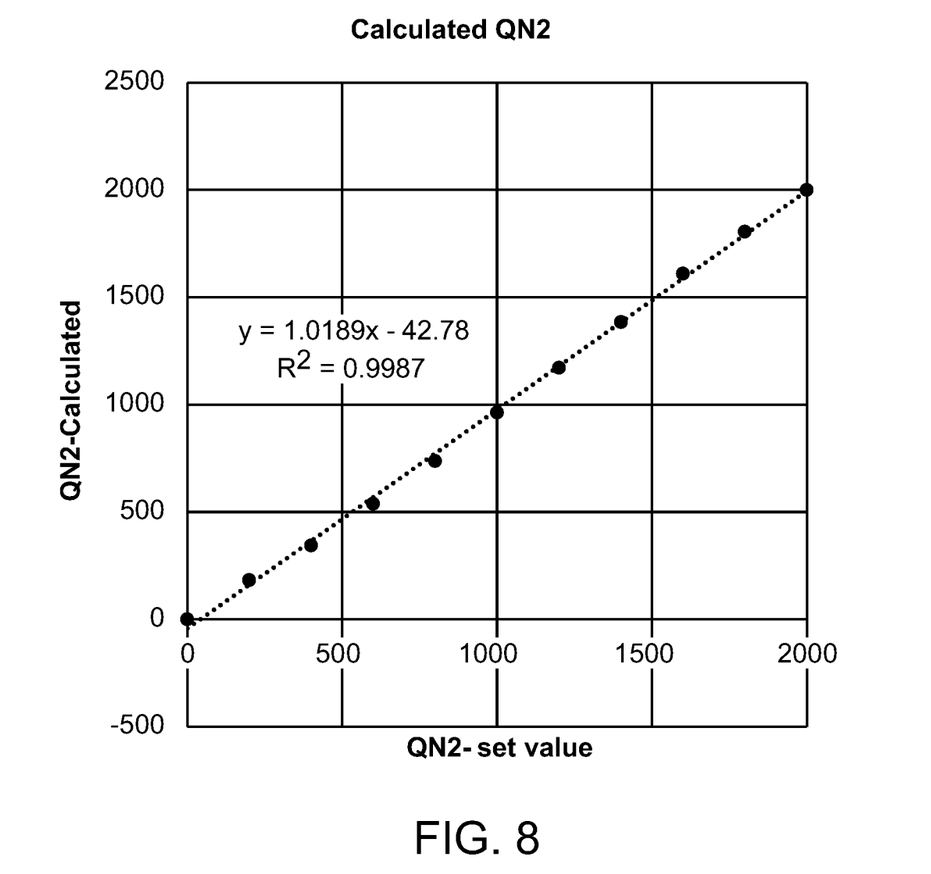
FIG. 8 is a graph of output measurements obtained from the experimental data shown in FIG. 7.

With a prototype setup as shown in FIG. 4, binary gas mixtures of nitrogen ($N_2$) and helium (He) were tested, the results of which are shown in FIGS. 7 and 8.

The experimental equipment is as described above with respect to Example 1 and a similar calibration procedure was performed to determine the determine species-dependent coefficient. restriction conductances and gas correction factors for helium and nitrogen. The obtained calibration data is shown below in Table 3.

TABLE 3

Calibration Data for Helium and Nitrogen

| Restriction Conductances | |
|---|---|
| $C_{N2}$ | 396.825397 |
| $C_{He}$ | 447.127208 |
| Gas Correction Factors | |
| $GCF_{N2}$ | 1.003225 |
| $GCF_{He}$ | 0.715465 |

Measurements of $Q_{MFM}$ and $P_T$ (also referred to as P2 in FIG. 4) were obtained and used to calculate $Q_a$ ($Q_{He}$) and $Q_b$ ($Q_{N2}$) according to Eqns. 20 and 21. The obtained measurements are shown in FIG. 6, the calculated values for $Q_{N2}$ are shown below in Table 4, and a plot of the results is shown in FIG. 7. In FIG. 7, the term "UUT" (Unit Under Test) refers to the mass flow meter of the setup.

TABLE 4

Binary Gas Analysis Results for Helium and Nitrogen

| $Q_{N2}$ | $Q_{N2}$ (%) |
|---|---|
| 1999.999935 | 100 |
| 1805.113348 | 90 |
| 1610.323372 | 81 |
| 1384.340413 | 69 |
| 1171.90125 | 59 |

TABLE 4-continued

Binary Gas Analysis Results for Helium and Nitrogen

| $Q_{N2}$ | $Q_{N2}$ (%) |
|---|---|
| 963.1156602 | 48 |
| 737.1834461 | 37 |
| 538.2373324 | 27 |
| 343.858187 | 17 |
| 182.9096418 | 9 |
| 0.000124891 | 0 |

The percentage concentration accuracies remained within 3% throughout the entire tested range. A larger difference in GCF between the gases provided larger flow ranges for measurement and high accuracy was obtained.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of analyzing a composition of a binary gas mixture, comprising:
   with a species-dependent mass flow meter, sensing a mass flow rate of a binary gas mixture comprising gases of differing gas correction factors;
   with a species-independent pressure sensor, sensing a total pressure of the binary gas mixture; and
   providing an output representative of a relative concentration of one gas of the binary gas mixture, the relative concentration determined as a function of the sensed mass flow rate and the sensed total pressure, wherein the function is in accordance with the following:

$$P_T = f_P(Q_a, Q_b, T)$$

$$Q_{MFM} = f_Q(Q_a, Q_b, T)$$

wherein $Q_a$ is a mass flow of a first gas of the binary gas mixture, $Q_b$ is a mass flow of a second gas of the binary gas mixture, T is a temperature of the gas mixture, $Q_{MFM}$ is the sensed mass flow rate, and $P_T$ is the sensed total pressure;

wherein $f_P$ and $f_Q$ are defined as follows:

$$P_T = f_P(Q_a, Q_b, T) = (k1 \cdot Q_a + k2 \cdot Q_b)T$$

$$Q_{MFM} = f_Q(Q_a, Q_b, T) = k3 \cdot Q_a + k4 \cdot Q_b + k5 \cdot T$$

where k1-k5 are constants.

2. The method of claim 1, further comprising determining the constants k1-k5.

3. The method of claim 1, further comprising maintaining a substantially constant volumetric flow of the binary gas mixture through a chamber.

4. The method of claim 3, wherein the chamber is evacuated by a constant volume pump.

5. The method of claim 4, wherein the function is in accordance with the following:

$$Q_a = (Q_{MFM} - GCF_b \cdot P_T \cdot S)/(GCF_a - GCF_b)$$

$$Q_b = P_T \cdot S - Q_a$$

where $Q_a$ is a mass flow of a first gas of the binary gas mixture, $Q_b$ is a mass flow of a second gas of the binary gas mixture, $GCF_a$ is a gas correction factor of the first gas, $GCF_b$ is a gas correction factor of the second gas, $Q_{MFM}$ is the sensed mass flow rate, $P_T$ is the sensed total pressure, and S is a pumping speed of the constant volume pump.

6. The method of claim 5, further comprising determining the pumping speed S.

7. The method of claim 1, further comprising determining a gas correction factor of each of the gases of the binary gas mixture.

8. The method of claim 1, wherein the output is a percentage volumetric flow of the one gas of the binary gas mixture with respect to a total volumetric flow of the binary gas mixture.

9. The method of claim 1, wherein the output is an alarm indicating the relative concentration of one gas of the binary gas mixture is above or beneath a threshold value.

10. The method of claim 1, wherein the species-dependent mass flow meter is a thermal mass flow meter.

11. A system for analyzing a composition of a binary gas mixture, comprising:
    a species-dependent mass flow meter configured to sense a mass flow rate of a binary gas mixture comprising gases of differing gas correction factors;
    a species-independent pressure sensor configured to sense a total pressure of the binary gas mixture;
    a controller configured to provide an output representative of a relative concentration of at least one gas of the binary gas mixture, the relative concentration determined as a function of the sensed total pressure and the sensed mass flow rate; and
    a chamber and an output pump, the output pump configured to evacuate the binary gas mixture from the chamber
    wherein the function is in accordance with the following:

$$Q_a = (Q_{MFM} - GCF_b \cdot P_T \cdot S)/(GCF_a - GCF_b)$$

$$Q_b = P_T \cdot S - Q_a$$

where $Q_a$ is a mass flow of a first gas of the binary gas mixture, $Q_b$ is a mass flow of a second gas of the binary gas mixture, $GCF_a$ is a gas correction factor of the first gas, $GCF_b$ is a gas correction factor of the second gas, $Q_{MFM}$ is the sensed mass flow rate, $P_T$ is the sensed total pressure, and S is a pumping speed of the output pump.

12. The system of claim 11, further comprising a temperature sensor and wherein the function is in accordance with the following:

$$P_T = f_P(Q_a, Q_b, T)$$

$$Q_{MFM} = f_Q(Q_a, Q_b, T)$$

where $Q_a$ is a mass flow of a first gas of the binary gas mixture, $Q_b$ is a mass flow of a second gas of the binary gas mixture, T is a temperature of the gas mixture as sensed by the temperature sensor, $Q_{MFM}$ is the sensed mass flow rate, and $P_T$ is the sensed total pressure.

13. The system of claim 12, wherein $f_P$ and $f_Q$ are defined as follows:

$$P_T = f_P(Q_a, Q_b, T) = (k1 \cdot Q_a + k2 \cdot Q_b)T$$

$$Q_{MFM} = f_Q(Q_a, Q_b, T) = k3 \cdot Q_a + k4 \cdot Q_b = k6 \cdot T$$

where k1-k5 are constants.

14. The system of claim 11, wherein the output pump is configured to maintain a constant volumetric flow of the binary gas mixture through the chamber.

15. The system of claim 11, wherein the mass flow meter is a mass flow controller, the mass flow controller configured to supply the binary gas mixture to a volume.

16. The system of claim 15, wherein the binary gas mixture is supplied to the volume at a rate that maintains a constant pressure of gases within the volume.

17. The system of claim 11, wherein the output is a percentage volumetric flow of the one gas of the binary gas mixture with respect to a total volumetric flow of the binary gas mixture.

18. The system of claim 11, wherein the output is an alarm indicating the relative concentration of one gas of the binary gas mixture is above or beneath a threshold value.

19. The system of claim 11, wherein the species-dependent mass flow meter is a thermal mass flow meter.

* * * * *